US00PP15261P3

(12) United States Plant Patent
Braun

(10) Patent No.: US PP15,261 P2
(45) Date of Patent: Oct. 26, 2004

(54) APPLE TREE NAMED 'BRAK'

(50) Latin Name: *Malus domesticus*
Varietal Denomination: Brak

(75) Inventor: Alois Braun, Girlan (IT)

(73) Assignee: Kiku G.m.b.H - S.r.l., Girlan (IT)

( * ) Notice: Subject to any disclaimer, the term of this patent is extended or adjusted under 35 U.S.C. 154(b) by 347 days.

(21) Appl. No.: 09/829,183

(22) Filed: Apr. 9, 2001

(65) Prior Publication Data

US 2001/0032345 A1 Oct. 18, 2001

(51) Int. Cl.[7] ..... A01H 5/00
(52) U.S. Cl. ..... Plt./168
(58) Field of Search ..... Plt./168, 161

(56) References Cited

U.S. PATENT DOCUMENTS

PP9,645 P * 9/1996 van Leuven ..... Plt./168
PP12,219 P2 * 11/2001 Torres ..... Plt./168

OTHER PUBLICATIONS

UPOV–ROM GTITM Computer Database, 2001/06, GTI Jouve Retrieval Software, citation for 'Brak'.*

* cited by examiner

*Primary Examiner*—Bruce R. Campell
*Assistant Examiner*—Susan B. McCormick
(74) *Attorney, Agent, or Firm*—Horst M. Kasper

(57) ABSTRACT

The present invention relates to a variety of an apple tree obtained by branch mutation and by selection of the variety 'Fuji'. The present invention variety exhibits an appropriate distinguishability, homogeneity, uniformity, and stability. The vigor of the tree is strong. The tree type is ramified. The habit of the apple tree is drooping. The pubescence on an upper half of a shoot is weak. The thickness as measured by the diameter at the center is medium for a dormant one year old shoot. The number of lenticels is many for one year old dormant shoot. The color of an unopened flower is light pink in a balloon stage. The surface of the fruit is colored red with a large number of small yellowish dots. Frequently the dots are disposed on curved lines with each line counting from about 4 to 8 dots.

2 Drawing Sheets

Latin name of the genus of the plant claimed: *Malus*.
Latin name of the species of the plant claimed: *Malus domesticus*.
Variety denomination: 'Brak'.

BACKGROUND OF THE INVENTION

1. Field of the Invention

The present invention relates to a novel apple tree.

2. Brief Description of the Background of the Invention Including Prior Art

A known variety of an apple plant is *Malus domesticus*. A variety of *Malus domesticus* is called 'Fuji'.

BRIEF SUMMARY OF THE INVENTION

A vegetatively propagated for variety of *Malus domesticus* is designated as 'Brak'. The variety has been bred by a branch mutation of the variety 'Fuji' by selection such that the variety 'Brak' exhibits necessary distinguishability, homogeneity, uniformity, and stability.

DETAILED BOTANICAL DESCRIPTION

Figure 1:
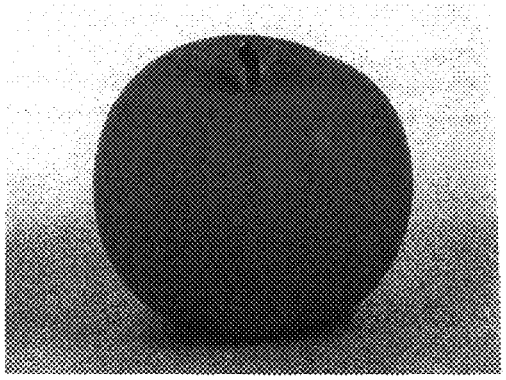
FIG. 1 is a side elevational view of a fruit of the apple tree.
Figure 2:
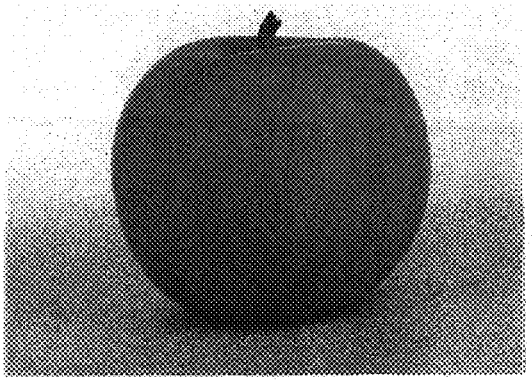
FIG. 2 is a side elevational view of another fruit of the apple tree.
Figure 3:
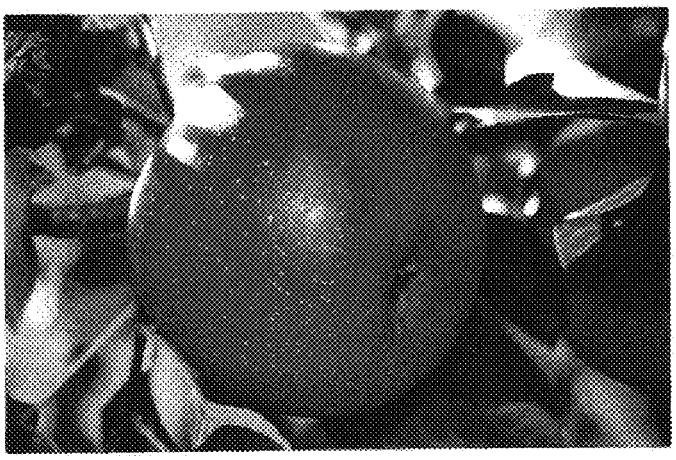
FIG. 3 is a perspective view of a hanging fruit of the apple tree showing part of the bottom of the fruit.
Figure 4:
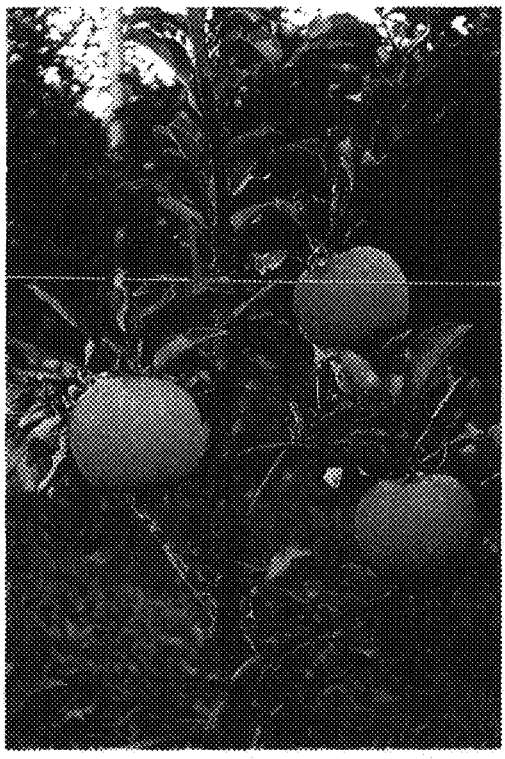
FIG. 4 is a side elevational view of three fruits hanging from an apple tree.
Figure 5:
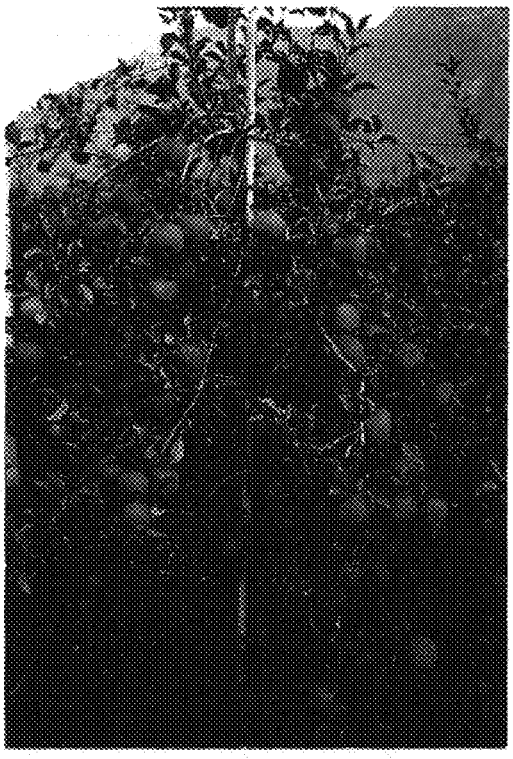
FIG. 5 is a view of an apple tree carrying a plurality of fruits.

The present invention relates to a variety of an apple tree. A branch mutation of the variety 'Fuji' has been performed by selection such that the present invention variety exhibits an appropriate distinguishability, homogeneity, uniformity, and stability.

The vigor of the 'Brak' tree is strong. The tree type is ramified. The habit of the 'Brak' apple tree is drooping. The pubescence on an upper half of a shoot is weak. The thickness as measured by the diameter at the center is medium for a dormant one year old shoot. The length of the internode is medium for a dormant one year old shoot.

The height of a one year tree is from about 1.7 m to 1.8 m. The height of a two year tree is from about 2.2 m to 2.5 m. The height of a five year tree is from about 3.2 m to 5.2 m. The height of the trunk of a two year old tree is from about 75 to 80 cm. The length of the branches of a one year old tree is from about 30 to 50 cm. The length of the branches of a two year old tree is from about 50 to 60 cm. The length of the branches of a five year old tree is from about 80 to 100 cm. The angle of the branches of a one to two year old tree is from about 35 to 45 degrees. The angle of the branches of a five year old tree is from about 55 to 60 degrees. The diameter of the trunk of a one year old tree is from about 12 to 16 mm. The diameter of the trunk of a two year old tree is from about 25 to 30 mm. The diameter of the trunk of a five year old tree is from about 50 to 55 mm.

The number of lenticels is many for one year old dormant shoot. The color of an unopened flower is light pink in a balloon stage. The size of the flower as measured by the diameter of the flower with petals pressed into a horizontal position is medium. The relative position of the margin of the petals is touching.

The main flower on terminal buds had a flowering time of eight days. The after flowering on one year old wood lasted 10 days. The attitude of the leaf relative to the shoot is outwards. The length of the leaf blade is medium. The width of the leaf blade is medium. The ratio length to width of the leaf blade is medium. The incisions of the margins of the leaf blade are serrated. The broad leaves disposed near the stem have 30 to 40 serrations on each of the two sides of the leaf. The elongated leaves disposed in the end regions of the shoots have about 50 serrations on each of the two sides of the leaf and a total of about 100 serrations for the whole elongated leaf. The length of the petiole is medium. The color of the petiole is FAN3 GREEN 138B.

The length of a leaf of a two year old tree is 8 cm. The length of a leaf of a five year old tree is 9.5 cm. The width of a leaf of a two year old tree is 4.5 cm. The width of a leaf of a five year old tree is 6 cm. The ratio of length to width of a broad leaf disposed near the stem of a two year old tree is from about 1.6 to 1.8. The length of a petiole or leafstalk of a two year old tree is from about 2.6 to 3.6 cm. The edge of the broad leaves disposed near the stem of a two year old tree is serrated with about 60 to 80 points total for a broad leaf. The length of a stalk of an apple of a two year old tree is from about 1 to 2 cm. The diameter or thickness of the stalk or stem of an apple of a two year old tree is from about 1.5 to 2 mm. The opening of the cavity of the calyx of a two year old tree is from about 2 to 2.5 mm. The opening of the cavity of the stem of an apple of a two year old tree is from about 2 to 2.5 mm.

The size of the fruit is large. The ratio of height to width of the fruit is medium. The position of the maximum width of the fruit is toward the stem or pedicel. The shape of the fruit is globose. The prominence of ribbing of the fruit is absent or very weak. The crowning at the calyx end is absent or very weak. The aperture of the eye or the calyx depression of the fruit is partly open. The size of the eye or calyx depression of the fruit is medium. The visual length of the sepal of the fruit is medium. The depth of the eye basin or calyx depression is deep. The width of the eye basin or calyx depression is broad.

The thickness of the stem or pedicel of the fruit is medium. The length of the stem or pedicel of the fruit is long. The depth of the stalk cavity or stem cavity of the fruit is medium. The width of the stalk cavity or stem cavity of the fruit is broad.

The relief of the surface of the fruit is smooth. The bloom of the skin of the fruit is absent. A greasiness of the skin of the fruit is absent. The color of the ground color of the skin of the fruit if visible is green yellow. The color of the over color of the skin of the fruit is red. The intensity of the color of the over color of the skin of the fruit is medium. The amount of over color of the skin of the fruit is very high. The pattern of over color of the skin of the fruit is striped. The amount of russet around are the eye basin or calyx depression of the fruit is absent or very low. The amount of russet on the cheeks of the fruit is absent or very low. The amount of russet around the stalk cavity or stem cavity of the fruit is low. The size of the lenticels of the fruit is medium.

The firmness of the flesh of the fruit as measured with a penetrometer is firm. The color of the flesh of the fruit is yellowish. The aperture of the locules for a median through locules of the fruit in cross-section is partly open.

The time of the beginning of flowering as measured by 10 percent open flowers is medium. The time of fruit ripening for eating is late.

The surface of the fruit is colored red with a large number of small yellowish dots. Frequently the dots are disposed on curved lines with each line counting from about 4 to 8 dots. The diameter of the dots is generally less then 0.5 mm and nearly always less then a millimeter. The total number of dots is estimated to be between from about five hundred to five thousand for a single fruit.

The edges of the leaves of the 'Brak' apple tree are serrated. The lenticels of the fruit are present in a high number of from about 5 to 8 per cm2 without forming a pattern. The diameter of the lenticels of the fruit are from about 0.6 mm to 1.1 mm. The number of lenticels increases in a direction toward the hollow of the calyx to 10 to 14 per $cm^2$ and the size of the lenticels decreases to from about 0.4 to 0.6 mm. The color of the lenticels of the fruit is FAN4 160B. The lenticels of the wood are clearly projecting, projections can be definitely felt upon palpating of the wood. Very many lenticels are present on the wood. The shape of the lenticels is dot like/circular up to globular/flattened. The lenticels on the trunk have a length of up to 2.2 mm and have a height of from 1 to 1.5 mm. In contrast, the lenticels on the branches are only from about 1.0 to 1.6 mm and are therefore smaller. The color of the lenticels on the trunk and on the branches is FAN4 155A to 155B. The stability of the propagation was considered. The tree 'Brak' shows a 99 percent variety originality in commercial installations. The so-called regression rate or reversion rate is only 1 percent. The typical properties of 'Brak' have not changed in the course of propagation. The observed plant retains its distinctive characteristics and reproduces true to type in successive generations. 'Brak' is reproduced by chip budding.

The leaves of 'Brak' have the following properties: The color of the top side of the leaf is FAN3 137A to 137B for younger trees. The color of the top side of the leaf is very dark 139A for older trees. The color of the bottom side of the leaf is FAN3, 137C to 138A for younger trees. The color of the bottom side of the leaf is 137C for older trees. The edge of the leaf is serrated. The number of serrated points is from 30 to 40. The ratio of the length to the width of a broad leaf disposed near the stem is from 1.5:1 to 1.6:1. The ratio of the length to the width of an elongated leaf disposed in an end region of a shoot is a about 2:1. The leaf has veins and there are on each side of the leaf 6 veins. The color of the veins on the bottom side of the leaf is FAN1 47B, the color is lighter toward the upper side up to FAN4 155B. The ratio of the length of the leaf (without petiole) to the length of the petiole is 2.2 to 2.5:1. The transition from the wood to the leaf has the color FAN4 178A.

The properties of the flowers of 'Brak' are: The number of the petals is five. The lehgth of a petal is about 20 millimeters ± 2 millimeters. The width of a petal is about 13 millimeters ± 1 millimeter. The ratio of length of a petal to width of a petal is about 1 to 1.5. The diameter of a flower as seen from above is about 36 millimeter ± 2 millimeter. The petals have light veins and are delicately subdivided. The color of the petal in the balloon state is light pink and on the outside FAN2 47A–47B.

The upper side of the petals is colored white and the lower side of the petals is colored light pink. The petals of the open flower exhibit a color FAN4 WHITE N155D plus slight traces of FAN2 47A–47B on the inside. The petals of the open flower exhibit a color FAN4 WHITE N155D plus slight traces of FAN2 47A–47B on the out side. The vessels of the pistil are erect and number from 10 to 12.

The reproductive organs have a length of 5.5 millimeter. The peduncle has a length of 17 to 20 millimeter and exhibits a color FAN3 GREEN 138B.

The flowers are average sensitive and average resistant against unfavorable weather conditions and freezing. The time of flowering is from April 10, to April 25 in South Tyrol depending on the climate.

The duration of flowering of 'Brak' is the same as has 'Fuji'. The time of duration from the flowering to the harvest is from about 170 to 180 days. 'Brak' is sensitive to the plant disease scabs. Diseases of the fruit include glassiness in case of over ripeness or, respectively, in case of a delayed harvest, which is a general problem of the varieties 'Fuji'. The apple 'Brak' has from about 8 to 12 kernels. Many chambers contain two kernels. The length of the kernels is from about 9.5 to 9.9 mm. The width of the kernel at the widest point is about 5.5 mm, which occurs at a distance of a third from the heart of the kernel. The width of the kernel at about two thirds of a distance from the heart of the kernel is about 3.5 mm. The thickness of the kernel of 'Brak' is from about 2.8 to 3 mm. The color of the kernel is FAN4 166C. Stripes or areas with darker color are present at the edges of the kernels and exhibit a darker color FAN4 166A to 166B. The interior of the kernel shows the color FAN4 155B.

The colors of the written description override the colors of the pictures. The colors were compared with The Royal Horticultural Society Colour Chart as follows: The bottom side of a leaf had the color FAN3, 137C.

The top side of a leaf had the color FAN3, 139A. The trunk of two year old trees had the color FAN4, N200B. The trunk of five year old trees had the color FAN4, N200C. The branches of the trees had the color FAN4, N200C. The lenticels of the trees had the color FAN4, 198D. The base color of the apple was FAN3, 144D. The color of the striping of the apple was FAN1, 45A. The color of the flesh of an apple fruit was FAN1, 13D. The color of the stalk or pedicel of an apple was FAN3, 144D. The color of a closed flower was FAN, N67C. The color of an open flower was FAN4, N155A. The color of the seeds was FAN4, 1663. The color of the cavity of the clayx was FAN3, 145A. The color of the cavity of the stalk or stem cavity was FAN 3, 145A. Two year old trees 'Brak' were observed at 30 cm away from the grafting location to have the color FAN4 177A and 130 cm away from the grafting location to have the color FAN4 177A to 177B. Six year old trees 'Brak' were observed to have the trunk color FAN4 201B and to have the color of fresh wood FAN4 177A. This means that during a young phase of the 'Brak' tree trunk and branches have the color FAN4 177A. The trunk and the old branches assume the color grey (FAN4 2013) more and more with increasing age, while the young wood (one to two years old) of the branches retains the color FAN4 177A.

A comparison was performed between 'Myra' (U.S. Plant Pat. No. 9,845) and 'Triple E' (U.S. Plant Pat. No. 12,219) and 'Brak'. An immediate comparison is difficult, since the climatic conditions are different and the environmental conditions are different. The color indications for 'Brak' and 'Triple E' are based on The R.H.S. colour chart, the color indications of 'Myra' are based on the Munsell color code. The covering color of the 'Brak' was Ruby red (45A). This color was observed under the same investigations in several research stations in Europe. The covering color of 'Myra' was pinkish red 39-12 to 39-13. The covering color of 'Triple E' was Red 53B. The striping of 'Brak' was uniform and not too wide. The striping of 'Myra' was slightly darker with pinkish-red stripes. 'Triple E' did not exhibit any stripes. The color development of the apple 'Brak' occurred late and only in the last weeks before harvesting time. The color development of the apple 'Myra' occurred 14 days earlier than that of standard 'Fuji' and there were red striped strains. The fruit maturation of 'Brak' was homogeneous. One can harvest almost all the crop of 'Brak' in a first picking because of uniform apples and because all 'Brak' apples have the same properties. Even those apples in the shadow areas of the tree and all apples 'Brak' have the same properties over the complete surface of the apple. This is associated with some advantages including a maximum of two pickings, uniform apples, better storage properties. The fruit maturation of 'Myra' apples was seven days earlier than the fruit maturation of red striped strains. The fruit maturation of 'Triple E' apples was 10 to 14 days before "BC2". The 'Triple E' apples growing in the shadow are more of a yellowgreen color (154C). The color of the 'Brak' leaves is very dark (139A). The color of the 'Myra' leaves is (21-14). The color of the 'Triple E' leaves is (138A). The ratio of the length to the width of the 'Brak' leaves is about 1.6:1 and the leaves are broad. The length of the 'Triple E' leaves is 8.4 cm and the width of 'Triple E' leaves is 3.2 cm. The color of the flesh of the 'Brak' apple fruit was (158A). The color of the flesh of 'Triple E' was (158D to 155D).

Comparison of the properties of 'Brak' with those of 'Fuji' apples: The point in time of flowering for 'Brak' is the same as the time of flowering of 'Fuji'. The growth speed of 'Brak' is the same as the growth speed of 'Fuji'. The leaf color of 'Brak' apples is dark green. The leaf color of 'Fuji' is light green. The leaf size of 'Brak' is large, the leaf size of 'Fuji' is medium. The tree habit of 'Brak' shows steep sticks. The tree habit of 'Fuji' shows more flat sticks. The vigor of the 'Brak' tree is strong. The vigor of the 'Fuji' tree is medium. The size of the lenticels on wood of the 'Brak' tree are large. The size of the lenticels on wood of the 'Fuji' tree are medium. The color of the flesh of the fruit of 'Brak' is yellow. The color of the flesh of the fruit of 'Fuji' is whitegreen. The color of the over-color of the skin of the 'Brak' fruit is brightly ruby-red. The color of the over-color of the skin of the 'Fuji' fruit is slightly orange-red. The pattern of the over-color of the skin of the 'Brak' fruit is striped. The pattern of the over-color of the skin of the 'Fuji' fruit is washed-out striped. The amount of the overcolor of the skin of the 'Brak' fruit is very high including in the shadow zone. The amount of the over-color of the skin of the 'Fuji' fruit is medium and in the shadow zone. the color is green. The brix of 'Brak' shows a high amount of sugar. The brix of 'Fuji' shows a lower amount of sugar. The percentage of salable fruits of 'Brak' is high (90 percent). The percentage of salable fruits of 'Fuji' is medium (40 percent). The fruits of 'Brak' growing up in the shadow are colored red. The fruits of 'Fuji' growing up in the shadow are colored green. A characterictic feature of the tree 'Brak' relative to the tree 'Fuji' is the ruby-red color of the fruit and the stripes of 'Brak'. All apples of the variety 'Brak' are colored over their complete surface, even those located in the shadow region of the tree. Particularly remarkable is the coloration of the 'Brak' apples in the cavity of the calyx and in the cavity of the stalk or stem cavity of the apples. Based on these features of the 'Brak' apples, there is one picking and a maximum of two pickings of the apples. The first picking harvests the largest part of the fruits. The harvest of the 'Brak' apples occurs with optimum inner values of the 'Brak' apple. The 'Brak' apple has a higher percentage of uniform and marketable product as compared to 'Fuji' apples. The 'Brak' apple exhibits a better storage behavior and for example less glassiness and less browncoloring of the fruit flesh as compared with 'Fuji' apples. The shelf-life of the 'Brak' apple is extended relative to the shelf-life of 'Fuji' apples. There is less rust formation with 'Brak' apples as compared with 'Fuji' apples. According to one characterizing feature of the 'Brak' apple, the 'Brak' apple tree generates in the first two years of harvesting apples with a brownish color and 'Brak' develops only in the third year its features relative to the apple fruit. It is another characterizing feature of the 'Brak' apple tree that the apples color relatively late on the tree as compared to the variety 'Fuji'. In a tree nursery, the 'Brak' tree has better rates of grafting in the course of asexual propagation, exhibits a stronger growth and a more uniform growing in comparison with a 'Fuji' tree. Seventy to eighty percent of the fruits are harvested in the first picking with 'Brak' trees. The part of uniformly looking and therefore marketable apples is higher as compared to 'Fuji'; from 63.6 to 74 percent of the apples are of a size from 80 to 90 mm. From about 61.1 to 86.5 percent of the 'Brak' apples are of good color. 'Brak' can be harvested at an optimum point in time of harvesting. 'Brak' has reached the highest coloration of the covering color at that point in time, where the scientifically determined optimum and ideal internal values of the fruit (pressure, sugar, acidity, starch) have been rached. This is in contrast not the case with 'Fuji': the 'Fuji' apples have to hang for a longer time on the tree, surpass the ideal harvesting values and therewith the optimum point in time of harvesting until the 'Fuji' apple reaches a red coloration. 'Brak' apples exhibit during storage less damages such as glassiness and brown discoloration of the flesh based on the optimum harvesting point in time, the 'Fuji' apples in comparison exhibit a higher glassiness. 'Brak' apples are not so rusted on the tree as are 'Fuji' apples.

The ruby-red covering color of the 'Brak' apples develops later on a comparative scale with 'Fuji' apples and in particular within the last four weeks prior to harvesting. The component of covering color of 'Brak' apples is at about 85 percent about twice as high as is the case with standard 'Fuji' apples.

The lenticels of 'Brak' on the wood of the trunk and of the branches are particularly characterizing and clearly distinguish a 'Brak' tree from a 'Fuji' tree. The leaves of the 'Brak' tree are darker as compared to the leaves of the 'Fuji' tree.

I claim:

1. A new and distinct variety of a 'Fuji' apple tree substantially as herein shown and described.

* * * * *

UNITED STATES PATENT AND TRADEMARK OFFICE

CERTIFICATE OF CORRECTION

PATENT NO. : PP 15,261 P2
APPLICATION NO. : 09/829183
DATED : October 26, 2004
INVENTOR(S) : Alois Braun It is certified that error appears in the above-identified patent and that said Letters Patent is hereby corrected as shown below:

--On the title page Item [50] should read
Varietal Denomination: Fuji Brak--.

Signed and Sealed this

Twenty-first Day of November, 2006

JON W. DUDAS
*Director of the United States Patent and Trademark Office*